United States Patent [19]

White et al.

[11] Patent Number: 5,591,914
[45] Date of Patent: Jan. 7, 1997

[54] ULTRASONIC POSITION SENSOR

[75] Inventors: Richard M. White; Stuart Wenzel; Eric R. Minami, all of Berkeley, Calif.

[73] Assignee: The Regents of the University of California, Oakland, Calif.

[21] Appl. No.: 480,162

[22] Filed: Jun. 7, 1995

Related U.S. Application Data

[60] Division of Ser. No. 902,713, Jun. 23, 1992, Pat. No. 5,450,752, which is a continuation-in-part of Ser. No. 399,865, Aug. 29, 1989, abandoned.

[51] Int. Cl.$^6$ ............................. H03B 5/30; G01B 11/14
[52] U.S. Cl. ............................. 73/643; 331/155; 356/373
[58] Field of Search ............................. 73/643, 655, 657, 73/579, 597; 331/155; 356/373

[56] References Cited

U.S. PATENT DOCUMENTS

| | | | |
|---|---|---|---|
| 3,476,483 | 11/1969 | Weeks | 356/256 |
| 3,854,325 | 12/1974 | Coate | 73/67.6 |
| 4,231,260 | 11/1980 | Chamuel | 73/597 |
| 4,484,820 | 11/1984 | Rosencwaig | 374/6 |
| 4,577,508 | 3/1986 | Chaplin | 73/655 |
| 4,624,142 | 11/1986 | Heyman | 73/597 |
| 4,752,917 | 6/1988 | Dechape | 367/125 |
| 4,833,928 | 5/1989 | Luukkala et al. | 73/862.39 |
| 4,928,527 | 5/1990 | Burger et al. | 73/657 |

FOREIGN PATENT DOCUMENTS

| | | | |
|---|---|---|---|
| 60-105925 | 6/1985 | Japan | 73/579 |
| 61-120925 | 6/1986 | Japan | 73/579 |

OTHER PUBLICATIONS

S. Wenzel, et al., "Ultrasonic–Oscillator Position Sensor," pp. 1–4, presented at the *IEEE Ultrasonic Symposium*, Oct. 1987, Denver, CO.

R. White, et al., "Ultrasonic–Oscillator Position Sensor," pp. 487–490, *Transducers '87*.

A. Young, et al., "A Twin–Interferometer Fiber–Optic Readout for Diaphragm Pressure Transducers," pp. 19–22, *IEEE* publication, Apr. 1988.

*Primary Examiner*—Hezron E. Williams
*Assistant Examiner*—Rose M. Finley
*Attorney, Agent, or Firm*—Fish & Richardson P.C.

[57] ABSTRACT

A position sensor for measuring the distance from a first position to a second position. The sensor may include an elastic wave generator, an acoustical path over which the elastic wave passes, and a transducer to which the wave passes. A measurement loop includes the acoustical path, and has electrical and optical elements. The electrical elements may compare the phases of the transducer signals from which the change in position between the first and second positions are determined. Alternatively, the measurement loop may comprise a feedback loop to produce oscillations and an output frequency. A frequency counter is included in the feedback loop to measure frequency.

2 Claims, 10 Drawing Sheets

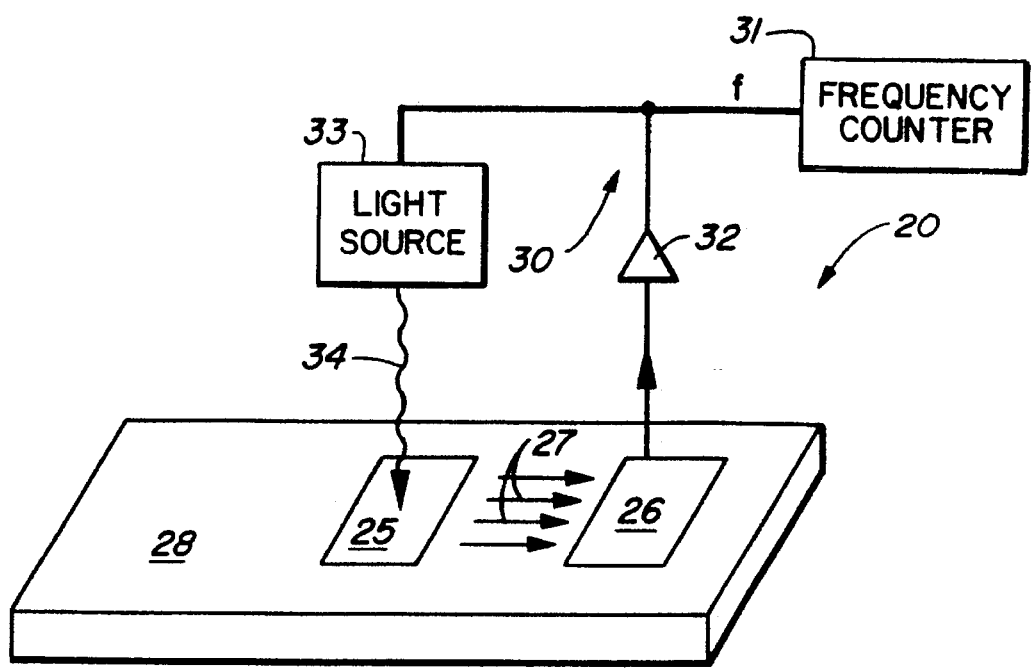
FIG._1.
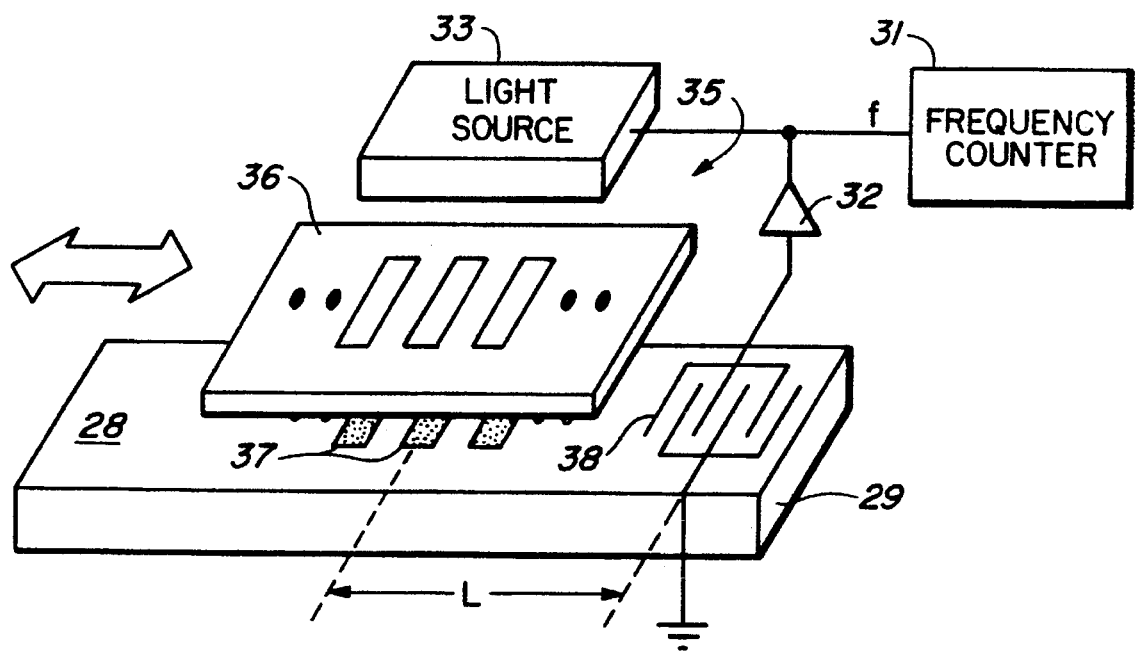
FIG._2.

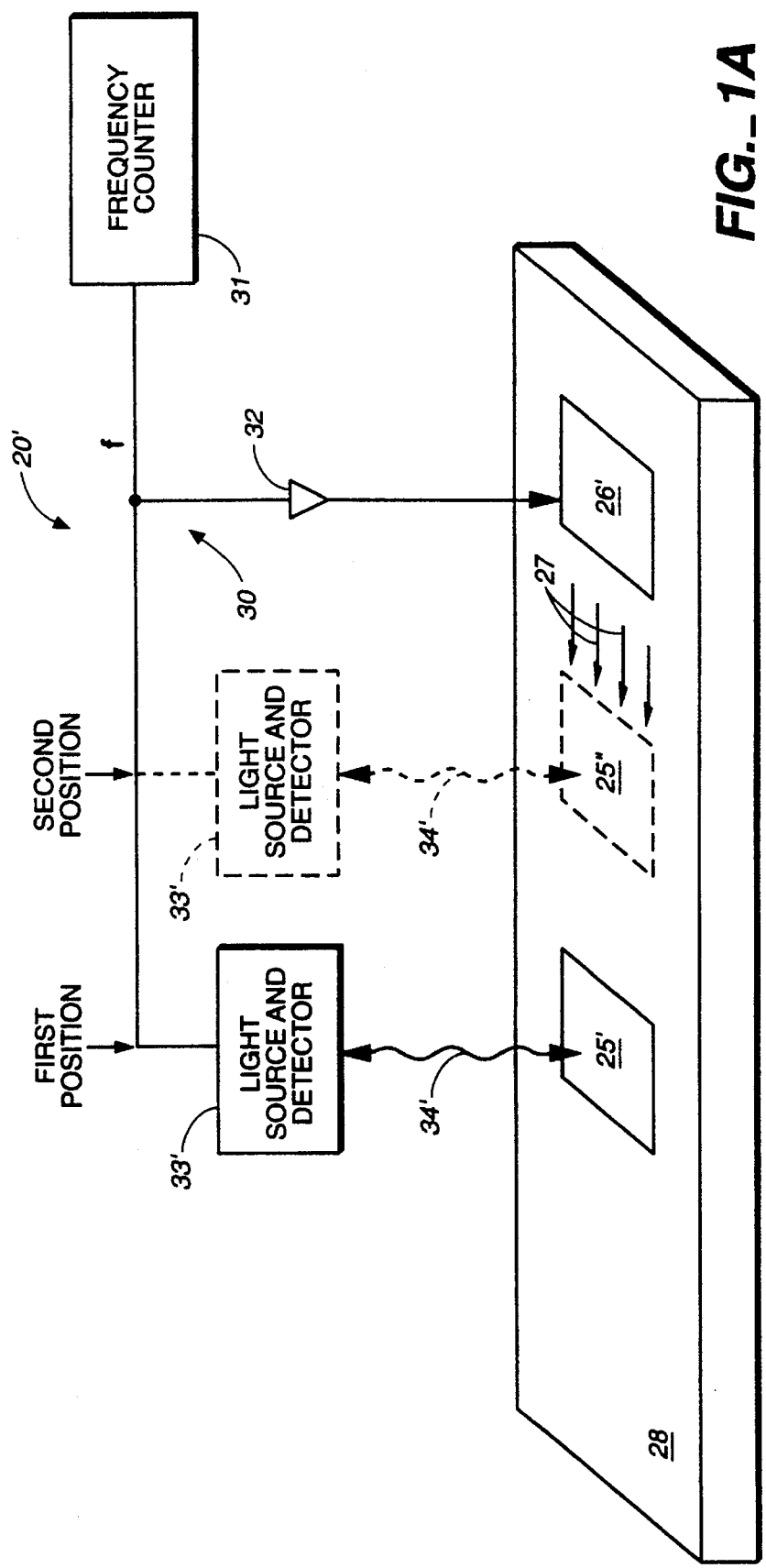
FIG._1A

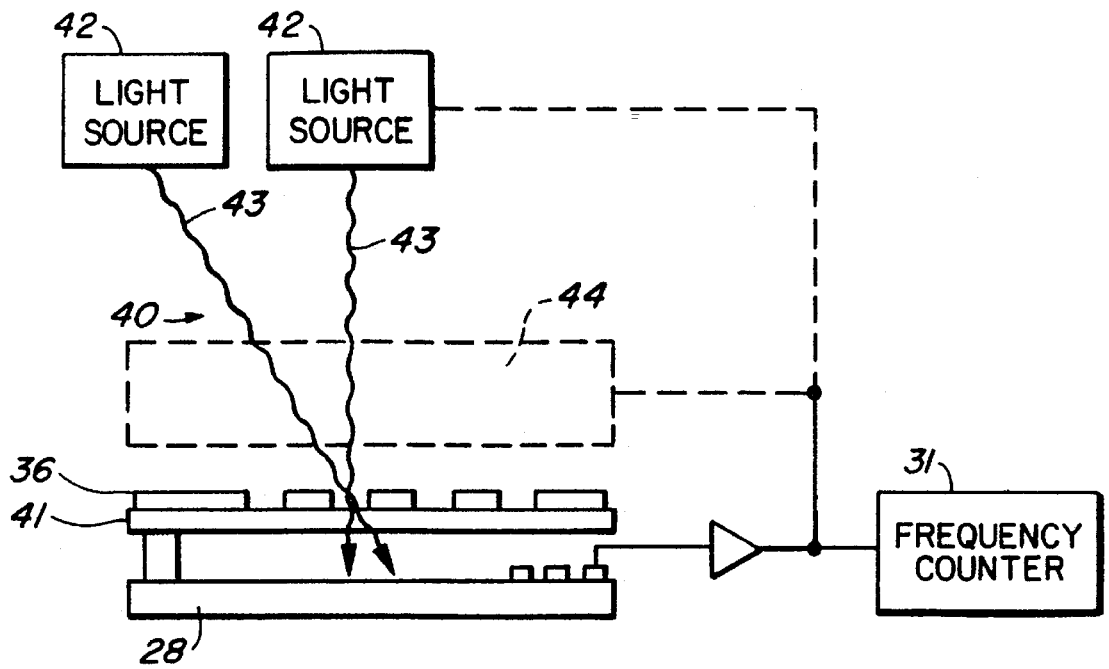
FIG._3.
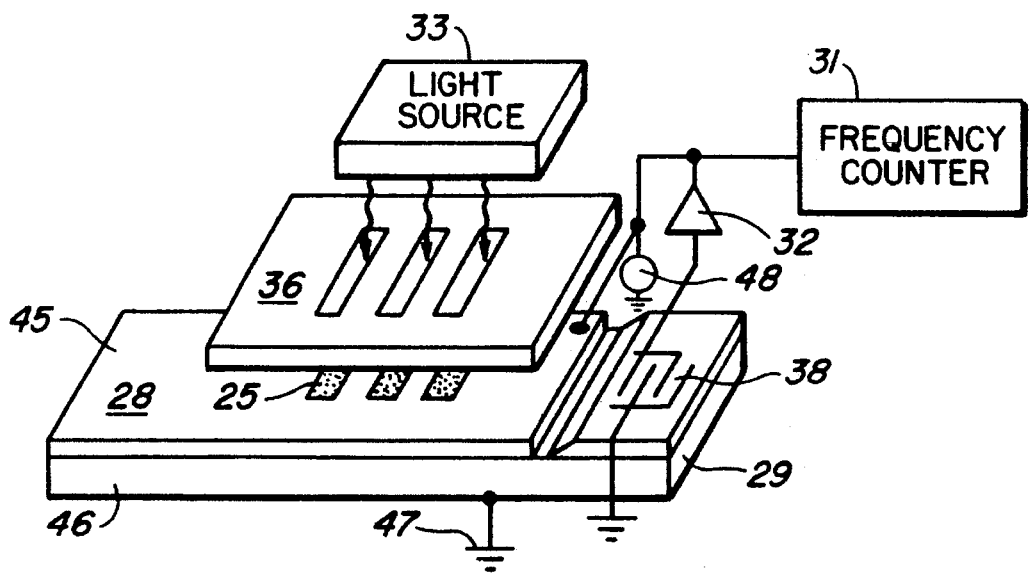
FIG._4.

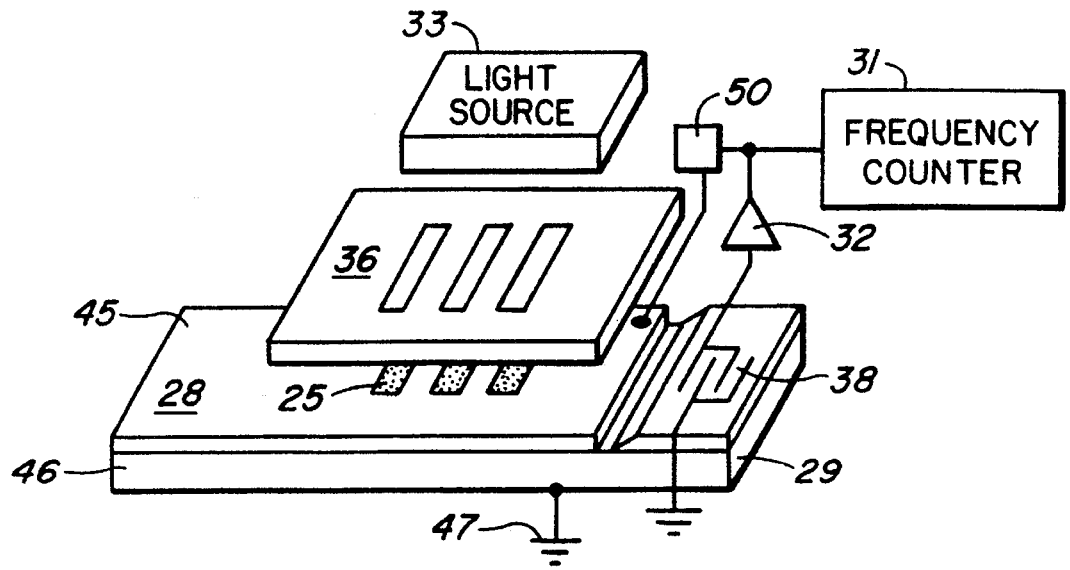
FIG._5.
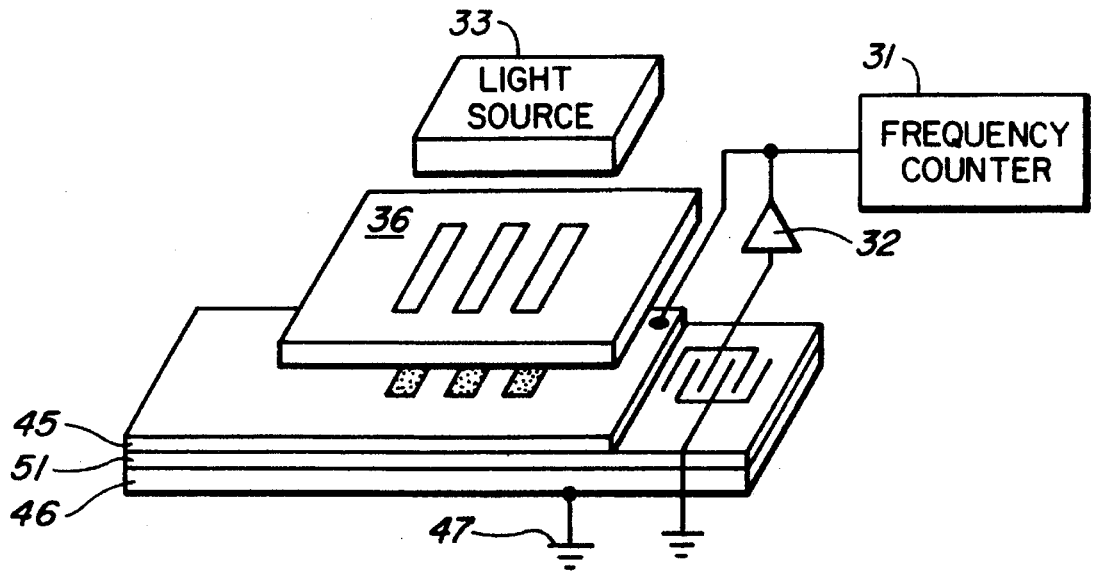
FIG._6.

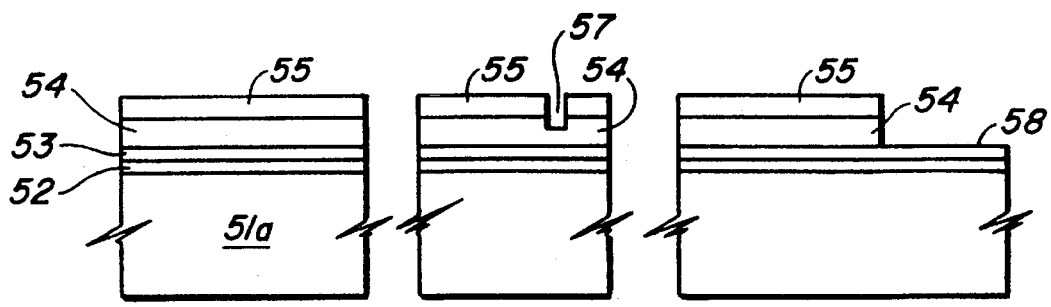
FIG._7.  FIG._8.  FIG._9.
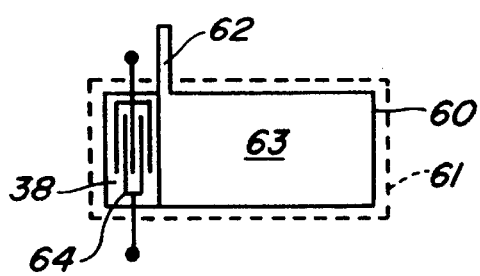
FIG._10.
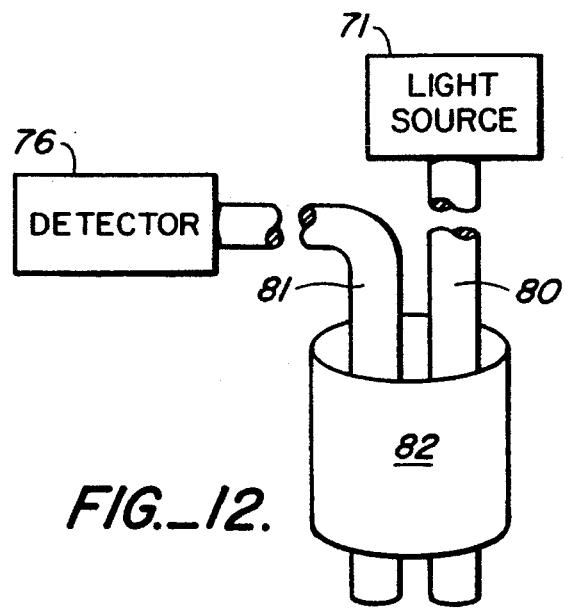
FIG._12.
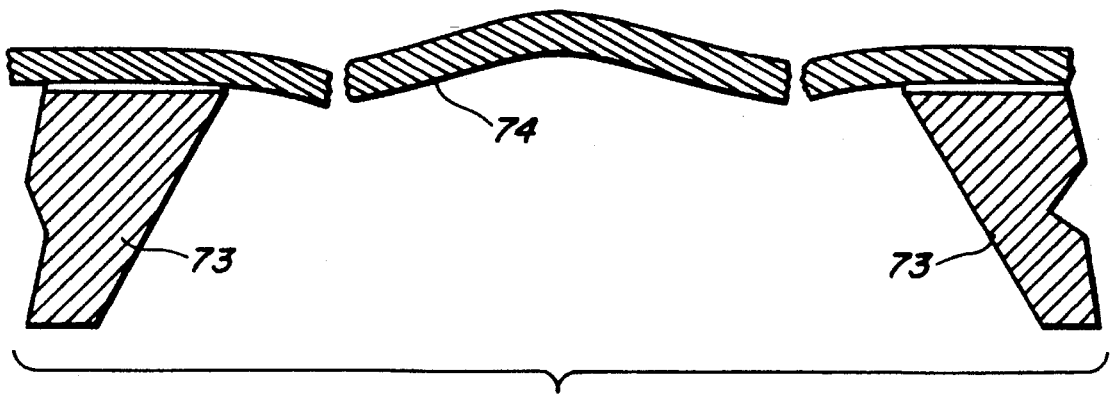
FIG._13.

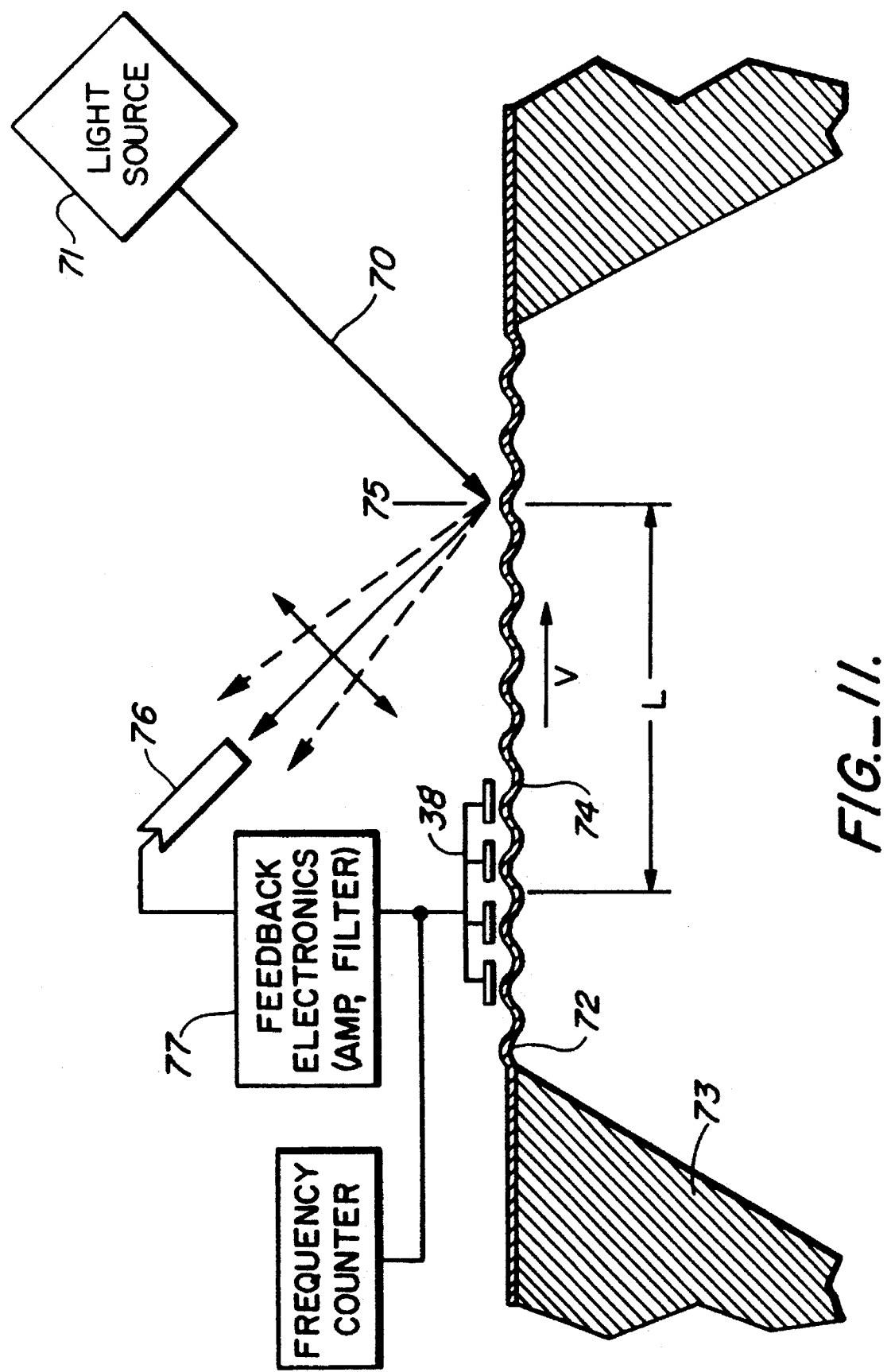
FIG._11.

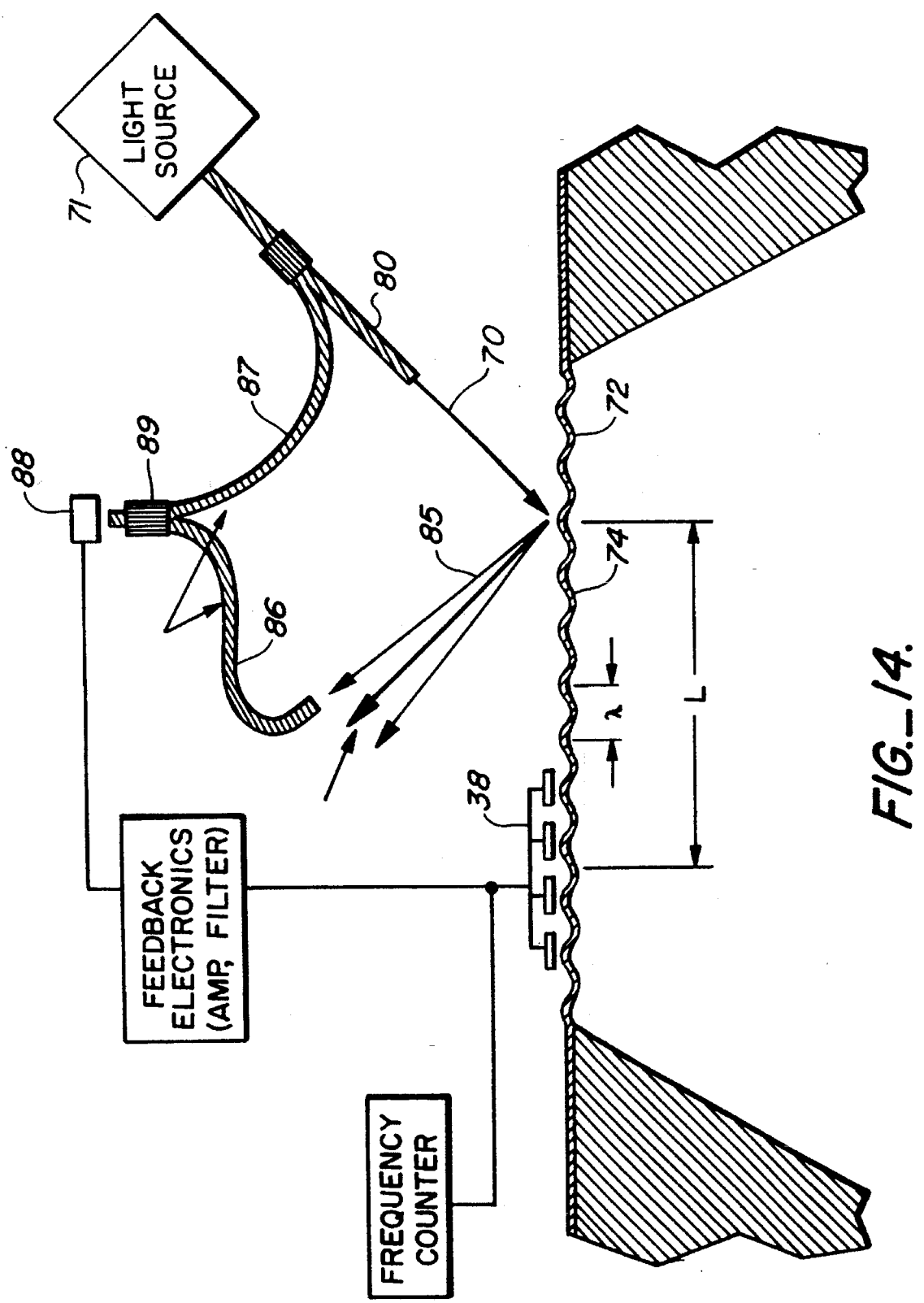
FIG._14.

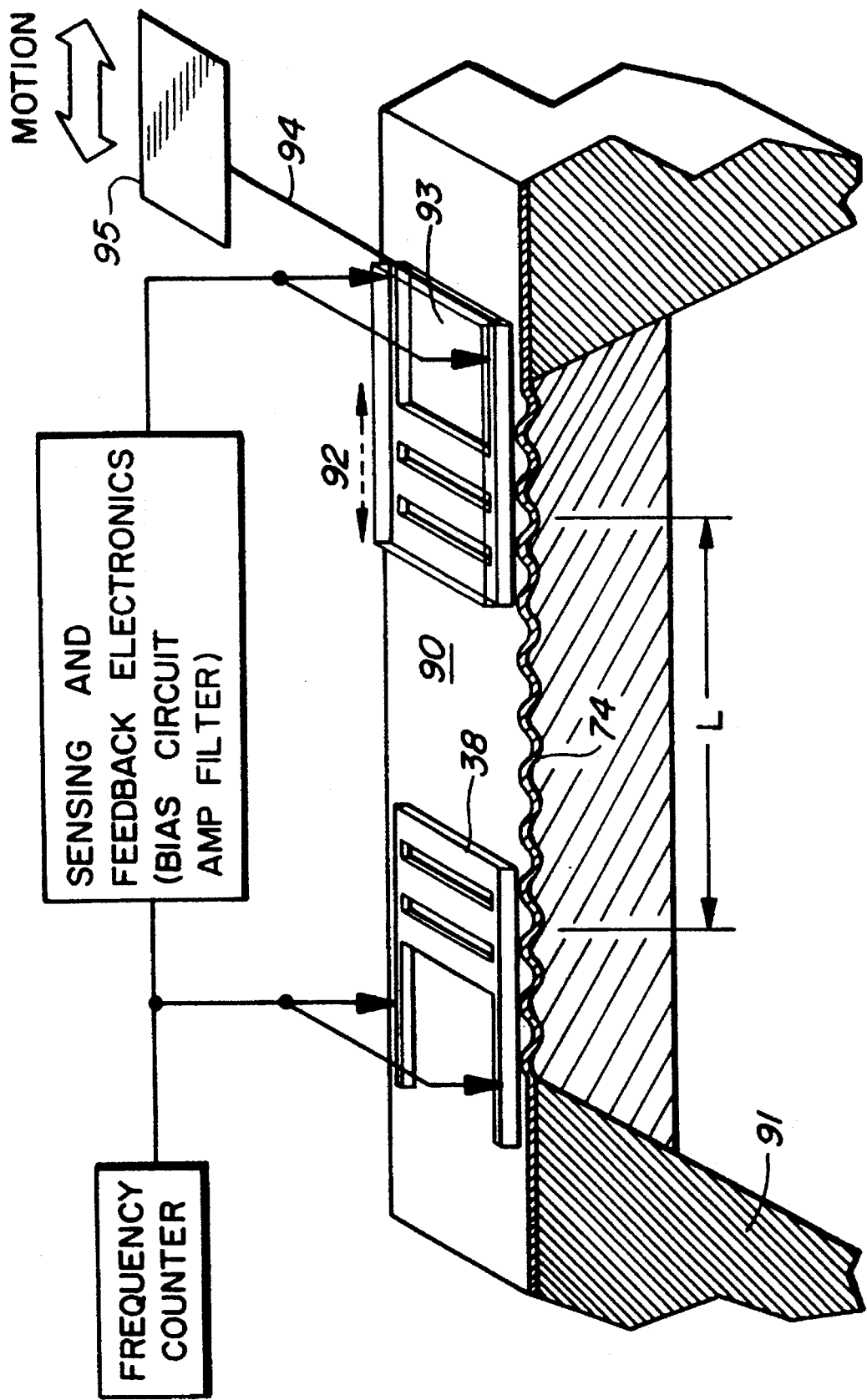
FIG._15.

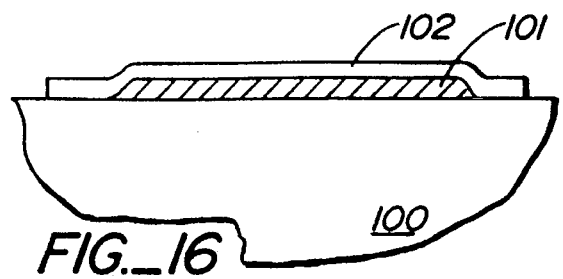
FIG._16
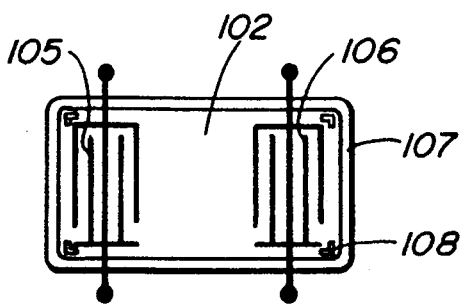
FIG._18
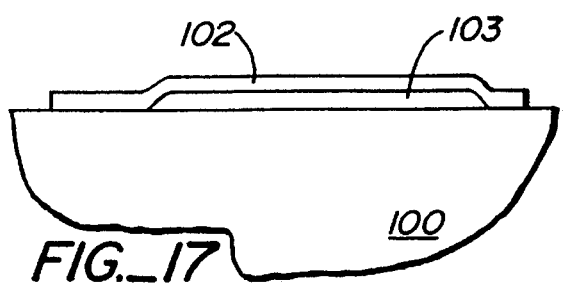
FIG._17
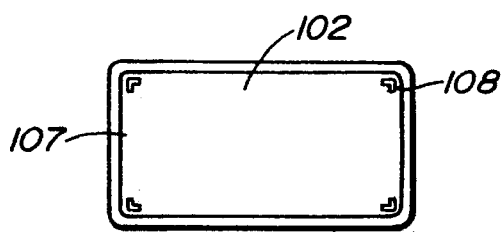
FIG._20
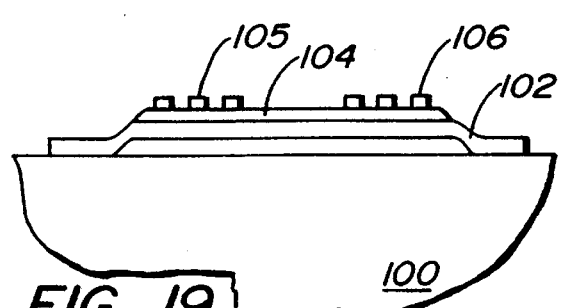
FIG._19
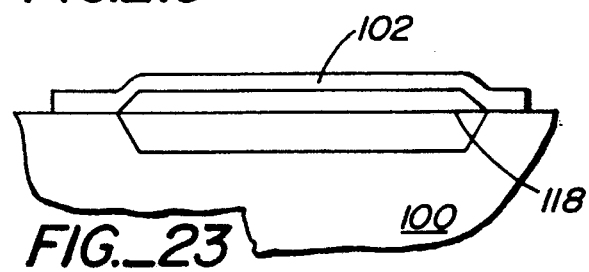
FIG._23
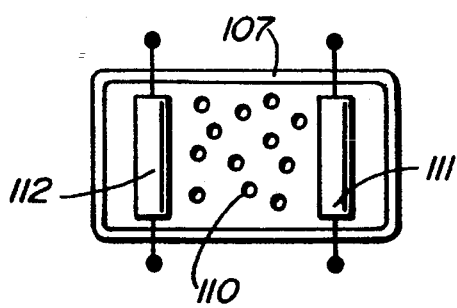
FIG._21
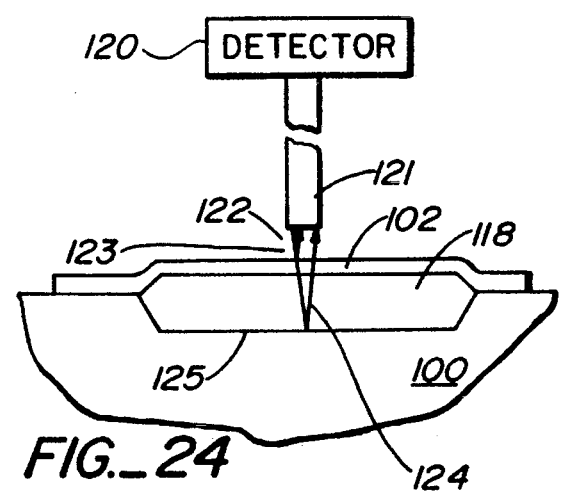
FIG._24
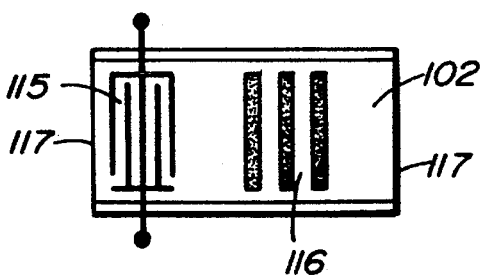
FIG._22

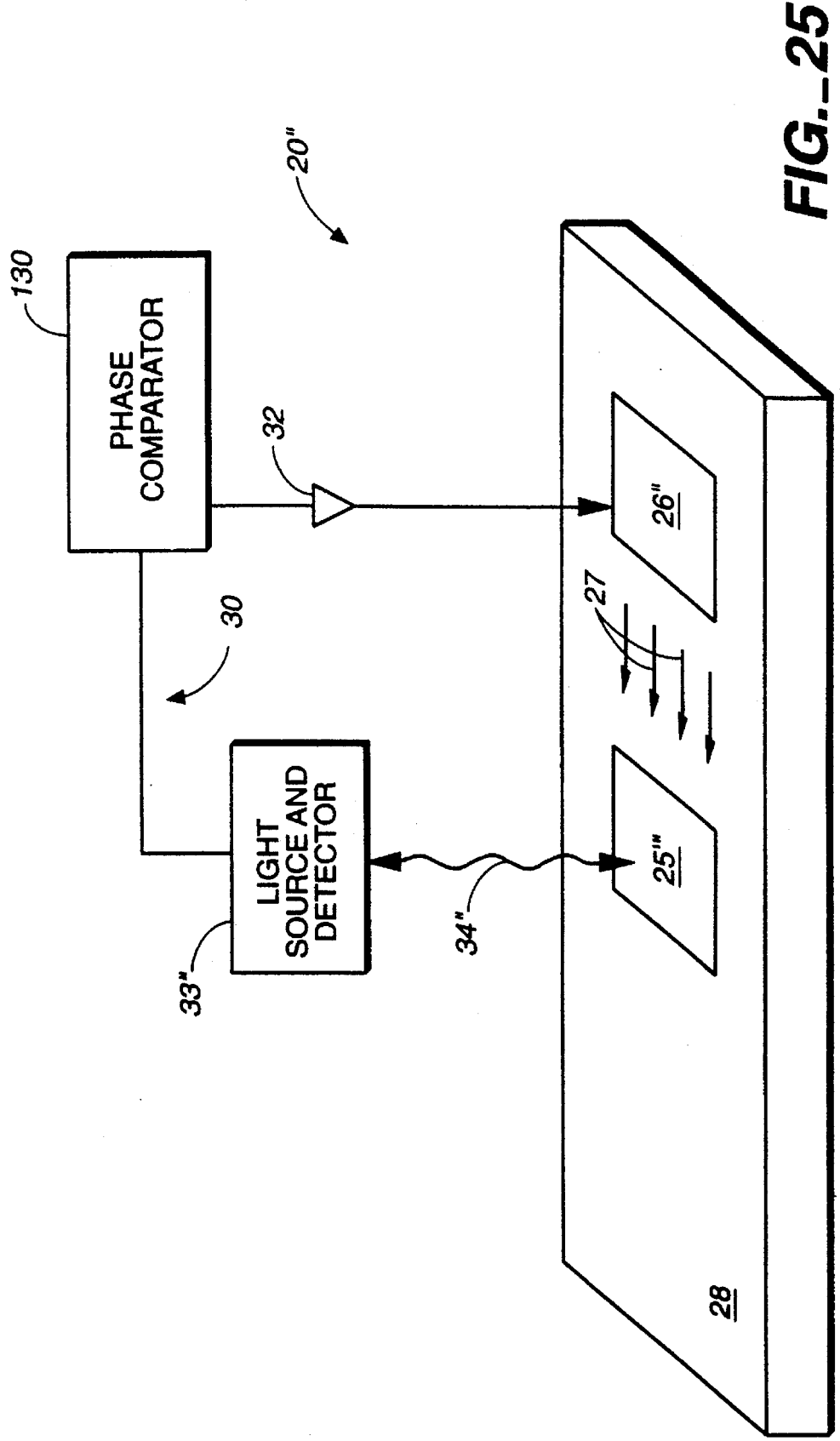
FIG._25

5,591,914

ULTRASONIC POSITION SENSOR

This is a division of application Ser. No. 07/902,713, filed Jun. 23, 1992, now U.S. Pat. No. 5,450,752, which is a continuation-in-part of application Ser. No. 07/399,865, filed Aug. 29, 1989, now abandoned.

BACKGROUND OF THE INVENTION

There are various ways of determining position both linearly and angularly, and they are covered in this invention. This determination is not as simple as taking a ruler and measuring, because some of the distances involved are very small, relating to multiples of angstroms rather than inches or yards or miles. The invention, in its linear aspects, is primarily for determining such very short distances.

The determination of angles is a matter that also involves small angles but can involve somewhat larger ones. The invention is useful in terms of small fractions of a radian as well as for larger angles.

SUMMARY OF THE INVENTION

The invention makes use of ultrasonic waves often in combination with light and frequency reading.

The invention makes use of both surface acoustic waves (SAW) and of Lamb waves. Both such types of waves enable movement over short distances to be converted into frequency changes occurring in the waves involved. Oscillations may be produced with a feedback loop that includes an acoustical path, electrical elements, and optical elements. The output frequency of the loop is determined by a frequency measurement done to produce the desired measurement of linear distances or angles.

In some forms of the invention, the motion of a movable spatial filter is employed and the distance moved thereby is determined by a frequency counter. At other times angular position is similarly determined, as will be explained.

The phase changes of signals may also be measured to detect relative movement.

How the elastic waves are used with electrical and optical elements in a feedback or measurement loop will be explained below.

BRIEF DESCRIPTION OF THE DRAWINGS

FIG. 1 is a diagram in perspective of a fundamental simple embodiment of the invention, employing elastic waves in combination with an acoustic path and optical elements and other operational elements to produce a position sensor embodying the principles of the invention.

FIG. 1A is a schematic illustration of a position sensor wherein a fixed transducer serves as a source of elastic waves.

FIG. 2 is a diagram similar to FIG. 1 in perspective of a linear position sensor embodying principles of the invention.

FIG. 3 is a diagram shown generally in section of a device used as an angular position sensor embodying principles of the invention. The light source and its beam are shown in two different positions.

FIG. 4 is a view in perspective of an embodiment somewhat like that of FIG. 2, showing the use of a steady light source in conjunction with a piezoelectric film as part of a linear position sensor.

FIG. 5 is a view similar to FIG. 4, except that it omits the piezoelectric film and uses the steady light source, in combination with a frequency counter, as a position sensor.

FIG. 6 is a view in perspective of another embodiment of a position sensor which employs principles of the invention. In this case a transparent conductor is used, together with an opaque substrate which is either piezoelectric or is coated with a piezoelectric film.

FIG. 7 is an enlarged view in section of a portion of the transparent conductor-substrate combination of FIG. 6.

FIG. 8 is a view similar to FIG. 7 of a somewhat different embodiment thereof.

FIG. 9 is a view similar to FIG. 8 of a still different embodiment of the combination of a transparent conductor and a substrate.

FIG. 10 is a plan view of a similar embodiment.

FIG. 11 is a sectional vertical diagrammatic view of an angle-modulation embodiment of the position sensor of the invention, showing optical detection of the waves.

FIG. 12 is a somewhat similar view of a modification of the embodiment of FIG. 11.

FIG. 13 is a simplified enlarged view similar to FIG. 11 of the FIG. 12 embodiment.

FIG. 14 is a vertical sectional view in diagrammatic form of a position sensor like that shown in FIG. 2 and involving the use of diffraction.

FIG. 15 is a diagrammatic view in perspective of a modified form of a position sensor of the invention, showing capacitive detection of waves according to principles of the invention.

FIG. 16 is an enlarged view in section of, or a portion of, a position sensor embodying the principles of the invention, shown at an early stage of manufacture.

FIGS. 17 through 24 continue the process of making the position sensor according to principles of the invention, showing various successive stages of the process begun in FIG. 15.

FIG. 25 schematically illustrates a position sensor in accordance with the present invention wherein the phases of the transducer signals are compared to measure position.

DESCRIPTION OF SOME PREFERRED EMBODIMENTS

An organizing principle that applies to various embodiments of this invention is outlined in FIG. 1, which shows a sensor 20. Elastic waves propagate from a left-hand opto-electric transducer 25 to a right-hand transducer 26 over an acoustic path 27 on a delay line 28. The transducer 26 is fixed and acts as a receiver of elastic waves. The transducer 25, as explained further below, is movable. The acoustical path 27 forms, together with electrical elements, and optical elements, a feedback loop 30 that produces oscillations with an output frequency f that is measured by a frequency counter 31. The electrical branch of the loop contains an amplifier 32 for providing sufficient gain to overcome transducer losses, attenuation in the acoustic path 27, and losses in the optical elements, such as in a light source 33 and the opto-electric transducer 25. The light source 33 may be combined with an optical modulator to produce either a steady or a modulated light beam 34.

The output frequency f provides a measure of the distance moved by an object, for example, to which light source 33 is connected. The light source 33 illuminates transducer region 25 on delay line 28. The location of region 25 changes in response to the movement of the object to which the light source is attached.

FIG. 1A shows a position sensor 20' wherein transducer 26' acts as a source or generator of elastic waves 27 in plate 28. The sensor provides an output frequency f that is a measure of the distance moved by an object to which light source and detector 33' are connected. Light source/detector 33' illuminates a region on plate 28 in which elastic waves can propagate; the illuminated region is denoted 25' for a first position of the source/detector and 25" for the second position of the source/detector (shown in phantom). Light propagating towards plate 28 and reflected from plate 28 is denoted 34'.

The light source/detector 33' produces a signal whose phase is related to the position of the light beam incidence on plate 28. The electrical output from the optical detector 33' is fed back through an amplifier 32 to transducer 26, forming a feedback loop that is capable of self-oscillation. Changes of the oscillation frequency are related simply to the distance between the first and second positions of light source/detector 33', and hence the distance moved by the object to which the source/detector is attached.

As an example, source/detector 33' might be attached to a movable stage of an optical microscope. The position sensor would then be used to indicate the distance the stage is moved between a first and a second position when one is examining an object, for instance. This arrangement, like the embodiment of FIG. 25 discussed below, in essence compares the phases of the transducer signals to detect relative motion of the transducers.

FIG. 2 embodies a linear position sensor 35. Motion of a movable spatial filter or mask 36, interposed between a substrate 29 in a delay line 28, and a modulated light source 33 causes a left-hand optoelectric transducer 37 to move relative to a fixed transducer 38 and to cause the oscillation frequency f of the feedback circuit to change. As an example of a typical application, the mask 36 may be attached to a moving stage used in semiconductor IC processing to position a photomask properly above a photoresist-coated wafer. The output frequency f may be measured by a frequency counter 31.

In the embodiment of FIG. 2, the substrate 29 may be a piezoelectric solid, such as quartz, or a non-piezoelectric solid with a piezoelectric coating, such as silicon coated with a thin film of zinc oxide. To realize an optically-produced transducer 37, special films may be required, as shown in FIG. 7 below.

FIG. 3 shows a structure substantially like that of FIG. 2 which may be used as an angular position sensor 40. Here, the mask 36 is attached by a support 41 to the delay line 28, so that the mask 36 is a small distance from the delay line 28. A light source 42 can move so that the "shadow" of the mask 36 falls on the delay line 28 at different locations as the light moves, two positions are drawn. In order to complete the feedback loop, a light beam 43 must be modulated at a frequency f. This can be accomplished either by modulating the light at its source 42 (for example, by current modulation), or by passing a steady light beam through an optical modulator 44 for chopping. Since the expected sensitivity of the linear sensor 35 is in the range of tens of angstroms, the angular sensor 40 appears to be able to determine angular shifts that are as small as $5 \times 10^{-7}$ radians (0.1 seconds of arc), assuming that the delay line 28 is about 100 micrometers from the apertures in the mask 36.

For economy and ease of operation, the use of a steady light source without an optical modulator is attractive. FIG. 4 shows schematically one way of doing this, by using spatially periodic heating. This system was described up to a point short of being fully enabling in two publications in 1987 (at Transducers '87 and at the Ultrasonics Symposium in October 1987—copies are enclosed with the Information Disclosure Statement filed with the subject application; the elements which were not described there are described below). In FIG. 4, as a steady (unmodulated) light beam 34 strikes the surface of the delay line 28, the light beam 34 does not carry information. The feedback loop is completed on the chip electrically.

FIG. 4 shows a position sensor in which the movable transducer 25 is formed by heating lighted regions by projecting light from the steady source 33 through the mask 36 onto a surface on the delay line 28 that responds to light and can give electrical energy to the photoelectric charge carriers (electrons) that are released when the light is absorbed. At its left-hand end, the delay line 28 is divided into two regions 45 and 46. The region 45 may be an optically transparent, electrically conducting film (such as indium-tin-oxide, or ITO), while the region 46 may be a photoconductor with a grounded ohmic contact 47 on its lower surface. A d-c potential (not shown) applied by the d-c source 48 to the top region 45 accelerates the carriers, increasing the resistive "$I^2R$" power dissipation in the delay line 28 and causing elastic wave generation by the thermoelastic technique, as described in the two aforementioned articles. Alternatively, the regions 45 and 46 may form a reverse-biased pn junction to which the bias is provided by a dc source 48.

To complete the feedback loop that operates at frequency f, heating is needed, set to occur at frequency f. If the thermoelastic effect is used, the heating is an "$I^2R$" effect, where the current per unit area flowing vertically in the structure is proportional to the product of the photoconductively-generated charge density with the accelerating voltage produced by the potential difference between the transparent conductor 45 and the underlying ground 46, 47. Thus, as shown in FIG. 5, if the voltage applied to the region 45 varies at frequency $f_1$, and the power dissipated per unit area will have its only alternating current component at frequency $2f_1$. Thus, a frequency divider 50 has been included in the feedback loop of FIG. 5, so that the fedback component is at the frequency $f_1$. In the case of a reverse-biased pn junction, the photoconductivity generated charge per unit area will be a function only of the light intensity and not of the bias voltage; hence in that case the frequency divider 50 can be omitted.

FIG. 6 shows an embodiment that may have a higher efficiency of wave generation than the embodiment employing the thermoelastic effect. Here, light passing through the movable mask 36 creates charge carriers in an underlying region 46 that cause any voltage impressed between the transparent conductor 45 and the ground connection 47 to appear across piezoelectric material 51 sandwiched between the regions 45 and 46. The appearance of this spatially periodic potential enables a voltage applied between the regions 45 and 46 to actuate the piezoelectric material 51. That voltage is obtained from the amplifier 32 directly, thus completing the feedback loop as required if oscillation is to occur.

FIG. 7 shows a cross-section through a typical composite film for realizing the optical transducer. The composite film is formed typically of a solid substrate 51a (typically silicon) or a supporting membrane 51a (typically silicon nitride), a ground plane 52 (typically aluminum), a piezoelectric layer 53 (typically zinc oxide), a photoconductive layer 54 (typically amorphous silicon), and a transparent electrical conductor 55 (typically indium-tin-oxide, ITO). The optically-defined transducer acts when light passes through the ITO 55 into the amorphous silicon 54, forming mobile charge carriers (photoconductivity) that couple potentials applied between the ITO 55 and the aluminum ground plane 52 close to the zinc oxide 53 in those regions that are illuminated. Since the electric fields are much weaker in the adjacent dark regions, elastic wave generation occurs preferentially in the piezoelectric film near the lighted regions.

To isolate sections of the ITO electrically, a groove 57 may be etched through the ITO layer 55 (typically by plasma etching), as shown in FIG. 8. If the depth of groove 57 is much smaller than the wavelength, elastic waves can pass through it without substantial interference.

In a region 58 (FIG. 9) where the immobile transducer is to be formed, the ITO layer 55 and the amorphous silicon layer 54 may be etched away entirely, as shown in FIG. 9.

As shown in FIG. 10, in order to permit the structure to adjust to the different tensile and compressive stresses that arise when these materials are deposited, a region 60 of a mostly uncoated membrane 61 may be left surrounding the structure. A narrow lead 62 provides for off-membrane contact to an ITO-covered region 63. The stationary transducer 38 may be located on a region 64 from which ITO and amorphous silicon have been removed.

FIG. 11 shows an embodiment where an optical link is employed in the feedback loop. An incident light beam 70 from a coherent or incoherent light source 71 is directed at a membrane 72 (in a silicon die or frame 73) on which Lamb waves 74 propagate. A reflected light beam 75 comprising the optical feedback link sweeps through a range of angles once per cycle of the wave, producing an amplitude-modulated current output from a detector 76. This current is amplified in an element 77 and fed back to a generating transducer 38, which couples piezoelectrically to the membrane 72 to produce the Lamb wave. We have found by experiments that the amplitude of Lamb wave motion can be quite large, and consequently that substantial angle modulation of an incident light beam could occur.

A vertical arrangement of input and output fibers is shown at an angle in FIG. 12 and would also be practical and possibly advantageous, since one would only have to align one member with respect to the membrane, rather than two. FIG. 12 shows an input fiber 80 and an output fiber 81 contained in a bundle of fibers 82. The angularly deflected beam that reflects from the surface as a result of the wave's passage over the membrane 74 in the die or frame causes the amplitude of the light picked up in the fiber 81 to vary at the wave frequency, as before. As with the embodiment of FIG. 11, the electrical output of the detector 76 is fed back to an amplifier and plastic wave frame.

FIG. 14 shows an embodiment somewhat similar to that of FIGS. 11 and 12, but where is detected a Nth order diffracted beam 85 produced when an unmodulated light beam 70 is incident upon a membrane 72 in which Lamb waves 74 are propagating. It is well known that a frequency shift occurs when a light beam at optical frequency v is reflected from a surface on which an elastic wave at frequency f is propagating: light beams having frequencies v±Nf emerge, each frequency beam emerging at its own characteristic angle. Thus, in FIG. 14 the Nth order beam (at frequency v+Nf, say) is incident on an optical fiber 86 and is transmitted to a detector 88 together with a sample of the reference beam (at frequency v) in a fiber 87, after being combined by an optical coupler 89. At the detector 88, these two beams interfere in known manner and produce an output current, at frequency Nf, that actuates the feedback electronics. The feedback loop is completed as the amplified output voltage is applied to the stationary generating transducer 38. If the N=1 frequency component is selected, by proper positioning of the pickup fiber 86, simple amplification will suffice. If N is different from unity, a frequency divider is needed to convert the frequency of the fed-back signal to frequency f again.

In this embodiment, very small horizontal translations of the input beam 70 are sensed. Such translations would be produced by translation of the input light source 71, or the input fiber 80, which might be coupled mechanically to an object such as a microscope stage whose motion is to be measured.

As shown schematically in FIGS. 11 and 14, and as explained above, generating transducers 38 are mechanically coupled to membrane or plate 74. As such, they do not move. Rather, the point at which light beam 70 strikes membrane 74 moves, for example, between a first and second position, in response to the movement of an object to which light source 71 is attached.

FIG. 15 shows a capacitive wave detection scheme that may be used as another embodiment of this position sensor. Here, the stationary transducer 38 is located on a piezoelectrically active thin membrane 90 in a silicon die 91 for propagation of Lamb waves 74. A movable transducer 92 is here realized as an electrically conducting array of strips that couple capacitively to the piezoelectrically-generated fields produced as the wave passes beneath the transducer structure 92. The electrode array 92 may be formed of a patterned aluminum film on the underneath side of an insulating member 93 (such as a glass slide) and is moved along the sensor surface because of the mechanical coupling 94 to a device 95 whose motion is to be detected, shown here as a positioning table that would be used in a semiconductor wafer fabrication apparatus.

FIGS. 16–24 show means for making membranes for Lamb wave devices (position and other types of sensors) by processing from one side of the wafer only. This avoids the additional time and cost involved in processing from both the top and bottom of a wafer so as to free the film that forms the membrane. This "frontside" structure also is stronger than the membrane structures in which membranes have been freed by etching entirely through the silicon wafer.

FIGS. 16, 17 and 19 are cross-sectional views showing steps to make a Lamb-wave sensor by only frontside processing. On a silicon wafer 100, a sacrificial layer 101 (FIG. 16) is formed and patterned. Typically this is a phosphorous-doped glass (phosphosilicate glass, or PSG). The film 102 is typically low-stress silicon nitride. This is to become a membrane. Upon etching away the sacrificial layer 101, a void 103 (FIG. 17) is formed, leaving a free-standing membrane 102. Onto it a layer of piezoelectric material 104 (typically zinc oxide) is grown (FIG. 19), and transducer electrodes 105 and 106 (typically aluminum) are formed.

FIG. 18 shows a top view of the membrane 102 with transducer electrodes 105 and 106. The membrane film 102 is attached to the silicon wafer 100 at lip or rim 107, which in this case entirely surrounds the membrane 102. In order to permit an etching solution to attack and dissolve the sacrificial layer 101, a plurality of access holes 108 are formed in the film 102 before etching. These etchant access apertures 108 are shown more clearly in FIG. 20. The holes 108 have been located outside the path that elastic waves will take on the finished membrane.

As it may be prudent to provide more access holes to speed up the etching process, one may put holes 110 in the wave path, as shown in FIG. 21, between transducers 111 and 112, provided the holes are small compared with the wavelength. Random spacing of the holes reduces the wave scattering effects. The holes may be made by photolithographic means, by particle track etching, electrolyte etchings, and by other means.

FIG. 22 shows a top view in which there is one fixed transducer 115 and one movable optically-produced transducer 116, in accordance with the present invention. In addition, in this case the left and right-hand ends 117 of the membrane 102 have been patterned, so that the ends do not contact the underlying silicon. Such an arrangement enables access of etchant to the sacrificial layer and also could be useful in sensor applications where a sensor is to be mounted in a flowing stream of liquid or gas; an example is a Lamb-wave sensor mounted in the sidewall of a pipe carrying gas whose pressure is to be measured.

In FIG. 23, the cavity formed by removal of the sacrificial layer 101 has been enlarged by etching into the underlying silicon with an etchant such as KOH. This forms a cavity 118 that can be useful in several ways. First, the cavity 118 may aid in preventing the membrane 102 from becoming attached to the underlying silicon 100, since the original cavity is typically only one or two micrometers deep, while the cavity 118 may be ten or more micrometers deep. Secondly, the structure may be very useful for pressure sensing, as in the scheme of FIG. 24, where pressure-induced changes of the height of the cavity 118 are sensed optically. Light from a source and a detection circuit 120 travels down an optical fiber 121 to the membrane structure. A light 122 is incident on the membrane 102, being partially transmitted and partially reflected. A reflected beam 123 returns to the optical fiber 121. A beam 124 transmitted through a transparent membrane 102 reflects from the bottom 125 of the cavity 118 and enters the fiber 121 after being retransmitted through the membrane after reflection. Interference between the reflected beams 123 and 124 is detected by an apparatus 120, which may contain a photodiode. Thus, pressure-induced or temperature-induced changes in the height of the cavity 118 are sensed to yield values of the pressure or temperature. This structure should be easier to position and use than the optically-read diaphragm pressure sensor recently described by Young et al., Hilton Head Workshop 1988.

Another embodiment of the present invention is shown in FIG. 25. This preferred embodiment involves the comparison of phases of the signals at two transducers. The phase comparison may be made by a phase comparator, such as a vector voltmeter.

As shown, position sensor 20" includes a transducer or transducing area 25'" and a fixed transducer 26". Light source/detector 33" illuminates (light beam 34") transducing area 25'", and transducer 26" serves as a source of elastic waves that propagate over path 27 to transducing area 25'". The area of transducer 25'" is small compared with the wavelength of the propagating elastic plate waves. The light/source detector 33" detects light (light beam 34") reflected by transducer 25'" and produces an electrical replica of the elastic waves received at transducer area 25'".

The manner in which light is reflected depends upon the instantaneous phase of the elastic waves propagating over acoustical path 27. The light source/detector 33" may be a solid-state laser diode (light source) and a photodiode (light detector), as used in a compact disc (CD) player, for example, with its electrical output signal connected to a phase change measuring device 130. The device 130 may be a phase comparator, such as a vector voltmeter, that indicates or determines the phase change of the output of detector 33" relative to that of the signal input, via amplifier 32, to generating transducer 26".

To those skilled in the art to which this invention relates, many changes in construction and widely differing embodiments and applications of the invention will suggest themselves without departing from the spirit and scope of the invention. The disclosures and the descriptions herein are purely illustrative and are not intended to be in any sense limiting.

What is claimed is:

1. A position sensor for measuring the distance between a first position and a second position of an object, comprising:

a structural member having an acoustical path over which elastic waves may propagate, transducer means for generating elastic waves in said structural member in response to an input signal, a light source spaced from said structural member for producing a light beam that can be directed to and reflected from a surface of said structural member wherein the light beam is reflected from said structural member in a manner that depends upon the phase of the elastic waves propagating over said acoustical path, an optical detector means for detecting said reflected light beam and for producing an output signal in response thereto, and a phase comparator means for detecting a phase change between said input and output signals to measure the distance between the first position and the second position of the object.

2. An apparatus, comprising:

a structural member having an acoustical path over which elastic waves may propagate, said structural member positioned relative to an object to provide a measure of a distance between a first position and a second position of the object, a first transducer means from which elastic waves on said structural member may be generated, a second transducer means to which the generated elastic waves pass, means for directing a light beam to said second transducer means wherein said light producing means provides a signal when illuminated by light reflected from said second transducer means, and a measurement loop, including said acoustical path, said light producing means and a means for comparing phases of a signal supplied to said first transducer means with the signal produced by said light producing means to measure the distance between the first position and the second position of the object.

* * * * *

UNITED STATES PATENT AND TRADEMARK OFFICE
CERTIFICATE OF CORRECTION

| | |
|---|---|
| PATENT NO. | : 5,591,914 |
| DATED | : January 7, 1997 |
| INVENTOR(S) | : Richard M. White et al. |

It is certified that error appears in the above-identified patent and that said Letters Patent is hereby corrected as shown below:

On the cover page of the patent, under "Inventors", delete the name of "Eric R. Minami".

Signed and Sealed this

Twelfth Day of August, 1997

*Attest:*

BRUCE LEHMAN

*Attesting Officer*     Commissioner of Patents and Trademarks